(12) United States Patent
Hur

(10) Patent No.: US 9,176,035 B2
(45) Date of Patent: Nov. 3, 2015

(54) SAMPLER

(75) Inventor: Dae Sung Hur, Seoul (KR)

(73) Assignee: NANOENTEK, INC., Seoul (KR)

( * ) Notice: Subject to any disclaimer, the term of this patent is extended or adjusted under 35 U.S.C. 154(b) by 100 days.

(21) Appl. No.: 14/349,368

(22) PCT Filed: May 15, 2012

(86) PCT No.: PCT/KR2012/003806
§ 371 (c)(1),
(2), (4) Date: Apr. 3, 2014

(87) PCT Pub. No.: WO2012/173342
PCT Pub. Date: Dec. 20, 2012

(65) Prior Publication Data
US 2014/0248197 A1    Sep. 4, 2014

(30) Foreign Application Priority Data

Jun. 14, 2011 (KR) .................. 10-2011-0057420

(51) Int. Cl.
| | |
|---|---|
| *G01N 1/28* | (2006.01) |
| *G01N 1/34* | (2006.01) |
| *G01N 33/49* | (2006.01) |
| *A61B 5/15* | (2006.01) |
| *B01L 3/00* | (2006.01) |

(52) U.S. Cl.
CPC ............... *G01N 1/34* (2013.01); *G01N 33/491* (2013.01); *A61B 5/1405* (2013.01); *A61B 5/150343* (2013.01); *A61B 5/150755* (2013.01); *B01L 3/502753* (2013.01); *B01L 2300/0681* (2013.01); *B01L 2300/0809* (2013.01); *B01L 2300/0832* (2013.01); *B01L 2400/0406* (2013.01); *B01L 2400/0478* (2013.01)

(58) Field of Classification Search
CPC .......... A61B 5/1405; A61B 5/150343; A61B 5/150755; B01L 2300/0681; B01L 3/502753
USPC ......................................... 422/527, 534, 535
See application file for complete search history.

(56) References Cited

U.S. PATENT DOCUMENTS

| | | | |
|---|---|---|---|
| 6,217,540 B1 | 4/2001 | Yazawa et al. | |
| 2006/0018798 A1* | 1/2006 | Sakaino et al. | ............... 422/101 |

FOREIGN PATENT DOCUMENTS

| | | |
|---|---|---|
| FR | 2735400 A1 | 12/1996 |
| KR | 10-2005-0030337 A | 3/2005 |

(Continued)

OTHER PUBLICATIONS

International Search Report for PCT/KR2012/003806 mailed Oct. 29, 2012 from Korean Intellectual Property Office.

*Primary Examiner* — Paul Hyun
(74) *Attorney, Agent, or Firm* — Paratus Law Group, PLLC

(57) ABSTRACT

The present invention relates to a sampler which is capable of rapidly and easily separating blood corpuscles from blood, being operated conveniently, and directly using extracted plasma. According to one embodiment of the present invention, a sampler includes a chamber and a membrane guide. Here, the chamber includes an insertion unit having an insertion hole on one side, wherein the other side is opened, and an inner side includes a receiving space for receiving a sample. Additionally, one side of the membrane guide is combined to the membrane, and the membrane guide includes a channel wherein filtered materials, which are filtered through the membrane among the samples received in the receiving space, are moved in a gravitational direction.

14 Claims, 20 Drawing Sheets

(56) References Cited

FOREIGN PATENT DOCUMENTS

| KR | 10-2006-0005390 A | 1/2006 |
| KR | 10-2007-0006904 A | 1/2007 |
| KR | 10-2009-0032409 A | 4/2009 |
| KR | 10-2011-0005963 A | 1/2011 |
| WO | WO 2008/097091 A1 | 8/2008 |

* cited by examiner (a)

(b)

SAMPLER

CROSS REFERENCE TO PRIOR APPLICATION

This application is a National Stage Patent Application of PCT International Patent Application No. PCT/KR2012/003806 (filed on May 15, 2012) under 35 U.S.C. §371, which claims priority to Korean Patent Application No. 10-2011-0057420 (filed on Jun. 14, 2011) which are all hereby incorporated by reference in their entirety.

TECHNICAL FIELD

The present invention relates to samplers, and more particularly, to a sampler that is capable of rapidly and easily separating blood corpuscles from blood, is convenient to manipulate, and allows extracted plasma to be directly used.

BACKGROUND ART

In general, a fluid sample analysis has been widely applied not only in the fields of chemistry and biotechnology but also the field of diagnosis using blood or body fluids collected from patients.

Recently, various small-sized analysis and diagnosis equipments and technologies thereof have been developed to more conveniently and efficiently conduct the fluid sample analysis.

One of important factors of the fluid sample analysis is preprocessing of a fluid sample.

Here, the processing of the fluid sample means, before the fluid sample analysis, extracting a desired amount of a sample, and then precisely processing the extracted sample, for example, in a dilution buffer at an appropriate rate or separating and refining the extracted sample by mixing the extracted sample with a reaction reagent that is in a solid or liquid state, filling the extracted sample with the reaction reagent, or using a support.

In general, to this end, the fluid sample is preprocessed using a pipette or a fountain pen filter. However, an amount of a sample to be preprocessed is very small and the sample should be very precisely preprocessed when a sample analysis is performed in a unit of a lab-on-a-chip or a lab-on-a-tip. Thus, it is not easy to precisely preprocess the very small amount of the sample using the pipette or the fountain pen filter.

Furthermore, in the case of a field inspection technique, a collected sample is preprocessed and injected again into a measurement device. However, an error occurs in the amount of the sample injected again.

Thus, there is a growing need to develop a sampler that is capable of minimizing errors in processing a tiny amount of blood or other samples and that is easy to manipulate so that even persons who are not specially educated or trained can handle it after listening to a brief explanation thereof.

DETAILED DESCRIPTION OF THE INVENTION

Technical Problem

To solve these problems, the present invention provides a sampler that is capable of easily and rapidly separating blood corpuscles from blood, is convenient to manipulate, and allows extracted plasma to be directly used.

Technical Solution

In accordance with the present invention, the above and other objects can be accomplished by the provision of a sampler comprising: a chamber in which an insertion unit having an insertion hole is formed at a side, another side of which is open, and in which a storage space is formed to store a sample; and a membrane guide, one side of which is coupled to a membrane, and which includes a channel in which a substance filtered from the sample stored in the storage space through the membrane moves in the direction of gravity.

The storage space storing the sample is formed between the membrane and an inner wall of the chamber in a direction of a plane of the membrane, and a direction in which the filtered substance passes through the membrane is different from the direction of gravity.

The channel comprises a microchannel, and the filtered substance moves due to at least one of a force of gravity and a capillary force.

A hydrophilic surface treatment is performed on the membrane guide.

The membrane guide comprises: a pressurizing portion formed to correspond to the storage space and including outer side surfaces to be in close contact with the storage space; a body portion which is formed at one side of the pressurizing portion, in which the membrane is disposed at both side surfaces thereof to cover the channel, and which is spaced a predetermined distance from wall surfaces of the storage space to allow the filtered substance to pass through the membrane and to be introduced into the membrane guide; and a discharging unit formed at another side of the pressurizing portion to be coupled to the insertion unit by being inserted into the insertion unit, and including an outlet passage therein to guide the filtered substance to be discharged.

In the body portion, a collecting portion is further formed by cutting some parts of the body portion, the collecting portion including both sides covered with the membrane to form a space in which the introduced filtered substance is collected, and connected to the outlet passage.

The outlet passage comprises a plurality of branched channels, one end of which is connected to the outlet passage and another end of which is connected to the collecting portion.

The collecting portion comprises a plurality of pillars such that a space of the collecting portion that is not connected to the outlet passage and the plurality of branched channels is filled with the plurality of pillars.

An auxiliary chamber into which the sample is primarily injected before being introduced into the storage space is further connected to one side of the chamber.

The auxiliary chamber comprises a connection portion to which a tube or a syringe storing a collected sample is directly connected.

The microchannel is formed at a central portion of the body portion in a lengthwise direction of the body portion by forming stepped portions to be stepped at both ends of side surfaces of the body portion in the lengthwise direction of the body portion.

A plurality of protrusions and a plurality of grooves are formed at a bottom surface of the microchannel in the lengthwise direction of the body portion.

Both ends of the membrane are attached to the stepped portions, respectively, such that the central portion of the membrane is spaced from the microchannel.

A fixed-quantity exhaust chamber is coupled to the insertion unit, the fixed-quantity exhaust chamber configured to store the filtered substance discharged via the insertion hole, and including an exhaust unit via which the stored filtered substance is exhausted when a push portion is pressed.

The fixed-quantity exhaust chamber is coupled to the insertion unit to be detachable from the insertion unit, and is replaceable with another fixed-quantity exhaust chamber including an exhaust unit, the internal diameter of which corresponds to an amount of the filtered substance to be discharged.

The exhaust unit is coupled to the fixed-quantity exhaust chamber to be detachable from the fixed-quantity exhaust chamber, and is replaceable with another exhaust unit, the internal diameter of which corresponds to an amount of the filtered substance to be discharged.

The push portion is integrally formed with an outer side surface of the fixed-quantity exhaust chamber to increase pressure in the fixed-quantity exhaust chamber when the push portion is pressed by an external force.

In accordance with the present invention, the above and other objects can be accomplished by the provision of a sampler comprising: a membrane guide in which a sample is stored in an inner space formed by a membrane covering side surfaces of the membrane guide, and that allows a substance filtered from the sample through the membrane to be discharged; and a chamber including an internal storage space into which the membrane guide is inserted via another side of the chamber that is open, and an insertion unit having an insertion hole and formed in a tubular shape at another side of the chamber to cause the substance filtered through the membrane to move in the direction of gravity and then be discharged.

A direction in which the filtered substance passes through the membrane is different from the direction of gravity.

A hydrophilic surface treatment is performed on the membrane guide.

The membrane guide comprises: a body portion covered with the membrane to be spaced a predetermined distance from wall surfaces of the storage space; a guide portion formed at a side of the body portion to correspond to the insertion unit to form a channel with inner side surfaces of the insertion unit and to guide movement of the filtered substance; and a discharging unit extending from an end of the guide portion to be spaced a predetermined distance from an inner side surface of the insertion unit, and configured to guide the filtered substance guided via the channel to be discharged via the insertion hole.

The channel comprises a microchannel, and the filtered substance moves due to at least one of a force of gravity and a capillary force.

A plurality of protrusions and a plurality of grooves are formed in at least one of an outer side surface of the guide portion and an inner side surface of the insertion unit in a lengthwise direction of the guide portion.

A fixed-quantity exhaust chamber including an exhaust unit is coupled to the insertion unit, wherein a through-discharge film is formed in the fixed-quantity exhaust chamber, and a fixed amount of the filtered substance is exhausted to the outside via the exhaust unit when a push portion of the chamber is pressed in a state in which the discharging unit passes through the through-discharge film.

The fixed-quantity exhaust chamber is coupled to the insertion unit to be detachable from the insertion unit, and is replaceable with another a fixed-quantity exhaust chamber including an exhaust unit, the diameter of which corresponds to an amount of the filtered substance to be discharged.

The push portion is integrally formed with an outer side surface of the chamber to increase pressure in the fixed-quantity exhaust chamber when the push portion is pressed by an external force.

A flange portion is formed on the open side of the chamber, and an auxiliary chamber is coupled to the flange portion such that inner side surfaces of the auxiliary chamber come in close contact with outer side surfaces of the flange portion, wherein a connection portion through which a tube or a syringe storing a collected sample is directly connected is formed on an upper surface of the auxiliary chamber.

Advantageous Effects

A sampler according to the present invention has the following effects.

First, a desired substance can be filtered, collected, and discharged from a sample, which is injected once, through a membrane in one step.

Second, a tube storing a collected sample can be directly inserted into a sampler without any manipulation, e.g., pipetting, thereby increasing user convenience.

Third, a surface area of a membrane can be increased to improve the separation yield and decrease a separation time, and the membrane is thus prevented from being blocked by the sample when a large amount of the sample passes through only some surfaces of the membrane.

Fourth, a sufficient amount of sample can be extracted even from a small amount of sample by setting a direction in which the sample passes through the membrane and a direction in which a filtered substance moves to be different and using both the force of gravity and a capillary force to move the filtered substance to be collected.

MODE OF THE INVENTION

Hereinafter, exemplary embodiments of the present invention will be described in detail with reference to the accompanying drawings.

Figure 1:
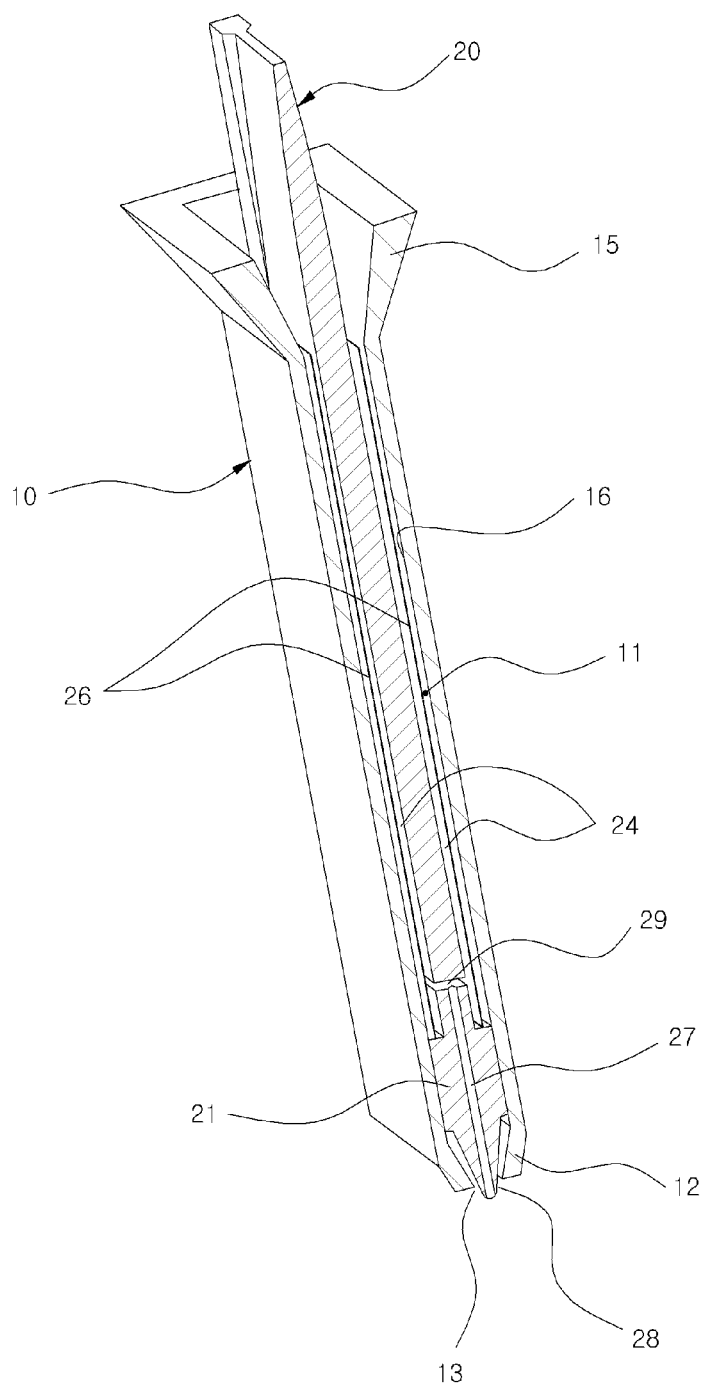
FIG. 1 is a cross-sectional view illustrating a state in which a chamber and a membrane guide of a sampler according to an embodiment of the present invention are combined with each other.
Figure 2:
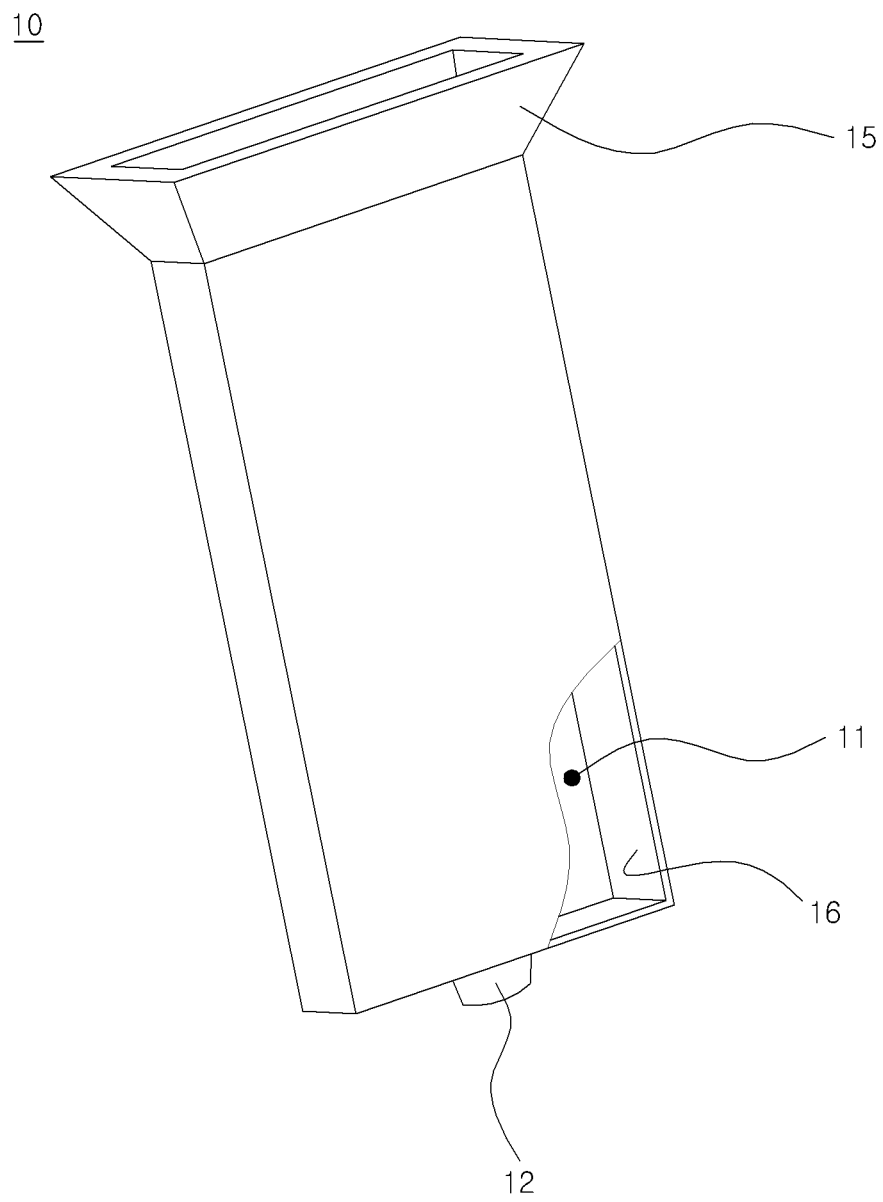
FIG. 2 is a perspective view of a chamber of a sampler according to an embodiment of the present invention.
Figure 3:
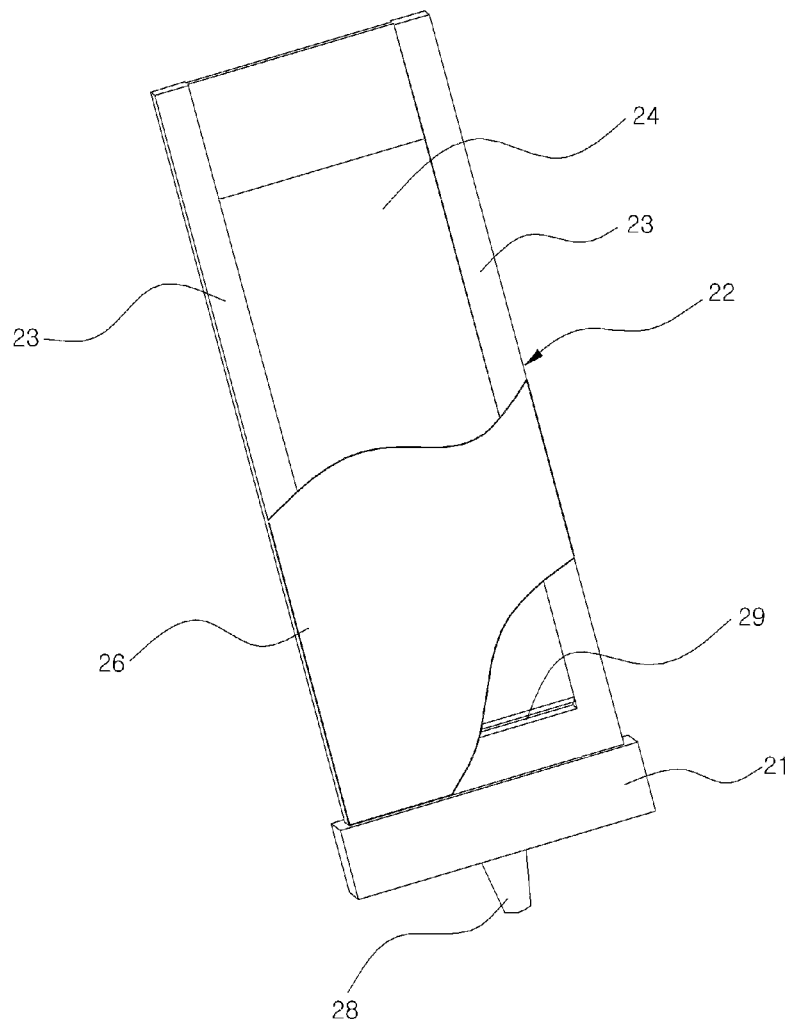
FIG. 3 is a perspective view of a membrane guide of a sampler according to an embodiment of the present invention.

FIG. 1 is a cross-sectional view illustrating a state in which a chamber and a membrane guide of a sampler according to an embodiment of the present invention are combined with each other. FIG. 2 is a perspective view of a chamber of a sampler according to an embodiment of the present invention. FIG. 3 is a perspective view of a membrane guide of a sampler according to an embodiment of the present invention.

As illustrated in FIGS. 1 to 3, the sampler may include a chamber 10 and a membrane guide 20. Here, a storage space 11 may be formed in the chamber 10 to store a sample, and an insertion unit 12 having an insertion hole 13 may be formed in one side of the chamber 10. The membrane guide 20 may be included in the storage space 11 such that an outlet 28 is fixed by being coupled to the insertion unit 12. A membrane 26 may be formed on an external surface of the membrane guide 20 to separate internal and external surfaces of the membrane guide 20, and allow only plasma, i.e., a substance to be filtered, of the sample to be introduced into the sampler through the membrane 26.

A channel 24 is formed in the membrane guide 20 to move the introduced filtered substance therein. The channel 24 may cause the filtered substance to move in the direction of gravity. To this end, the sampler that is a combined structure of the chamber 10 and the membrane guide 20 may be placed on a predetermined rack (not shown) in a state in which the sample is injected into the sampler. The channel 24 may be formed to move the filtered substance in the direction of gravity in the state in which the sampler is placed on the predetermined rack.

The channel 24 may be a microchannel through which a capillary force is additionally applied to move the filtered substance to be discharged via the outlet 28.

Specifically, in the present embodiment, the storage space 11 is formed in the chamber 10.

One side of the chamber 10 may be blocked, the insertion unit 12 is formed at a center of the blocked side of the chamber 10, and the insertion hole 13 is formed in the insertion unit 12.

Thus, the storage space 11 is connected to the outside via the insertion hole 13.

Another side of the chamber 10 is open to be connected to the outside.

That is, one end of the storage space 11 formed in the chamber 10 is connected to the outside via the insertion hole 13 and another end of the storage space 11 is connected to the outside via the open side of the chamber 10.

The membrane guide 20 may be inserted into the storage space 11 to be coupled to the storage space 11. In this case, the membrane guide 20 is inserted into the storage space 11 via the open side of the chamber 10.

In this case, an introduction unit 15 may be formed at the open side of the chamber 10.

The introduction unit 15 may outwardly extend to be open. Through the introduction unit 15, the membrane guide 20 may be guided to be smoothly inserted into the storage space 11.

The membrane guide 20 may include a pressurizing portion 21, a body portion 22, and the outlet 28.

First, the pressurizing portion 21 is inserted into the storage space 11 via the open side of the chamber 10.

Here, all of outer sides of the pressurizing portion 21 may be in close contact with wall surfaces 16 of the storage space 11.

The body portion 22 may be formed at one side of the pressurizing portion 21. In this case, the pressurizing portion 21 and the body portion 22 may be integrally formed with each other.

Also, the body portion 22 is formed to entirely correspond to the storage space 11, and outer side surfaces of the body portion 22 may be formed to a thickness that causes the body portion 22 to be spaced a predetermined distance from the wall surfaces 16 of the storage space 11.

Stepped portions 23 may be formed at both side surfaces of the body portion 22, and particularly, at spacious ends of both the side surfaces of the body portion 22 in a lengthwise direction of the body portion 22.

The stepped portions 23 may be stepped to be higher than the both side surfaces of the body portion 22.

Thus, in the body portion 22, the stepped portions 23 may be formed at both ends and the channel 24 having a surface that is lower than the stepped portions 23 may be formed at the center.

Also, the membrane 26 is attached to the stepped portion 23.

Here, both ends of the membrane 26 may be attached to the stepped portions 23, respectively, and the membrane 26 may be disposed at both side surfaces of the body portion 22.

Also, the membrane 26 may be attached to cover a most part of the channel 24, and a central portion of the membrane 26 may be spaced from the channel 24.

The outlet 28 having an outlet passage 27 may be formed at another side of the pressurizing portion 21.

Here, the outlet 28 may be formed to correspond to the insertion hole 13. Thus, the outlet 28 may be coupled to the insertion hole 13 by being inserted into the insertion hole 13.

In this case, the outlet 28 inserted into the insertion hole 13 may extend to and protrude from the outside of the insertion unit 12.

Thus, when the membrane guide 20 is inserted into the storage space 11 via the open side of the chamber 10 and is then continuously pressurized, the outlet 28 is fixed while being coupled to the insertion unit 12.

In this case, all of the outer side surfaces of the pressurizing portion 21 are in close contact with the wall surfaces 16 of the storage space 11.

Since the body portion 22 is spaced the predetermined distance from the wall surfaces 16 of the storage space 11, a clearance space is formed in the storage space 11.

The storage space 11, i.e., the clearance space, in which the sample is stored is formed between inner walls of the membrane 26 and the chamber 10 in a direction of a surface of the membrane 26. Thus, a surface area of the membrane 26 that the sample contacts may increase, and the membrane 26 may be thus prevented from being blocked by the sample when a large amount of the sample passes through only some surfaces of the membrane 26.

When the sample is introduced into the clearance space, the sample contacts a large area of the membrane 26.

In this case, the membrane 26 may be formed to have multiple holes, the diameters of which become smaller in a direction from an outer side of the membrane 26 that contacts the sample to an inner side of the membrane 26 opposite to the channel 24.

Thus, some of the sample is filtered through the membrane 26 and introduced into the sampler. In the present embodiment, a direction in which the sample is filtered, i.e., a direction in which the sample passes through the membrane 26, is set to be different from the direction of gravity. That is, in the present embodiment, when the sampler is placed on the predetermined rack, the direction in which the sample passes though the membrane 26 is substantially perpendicular to the direction of gravity. However, the direction in which the sample passes though the membrane 26 may be set to form a predetermined angle that is not perpendicular to the direction of gravity.

The substance filtered as described above moves in the channel 24 due to the force of gravity. When the channel 24 is a microchannel, a capillary force is additionally applied to the filtered substance, thereby causing the filtered substance to move in a direction, e.g., a downward direction.

That is, in the present embodiment, the filtered substance may move due to the force of gravity, a capillary force, or both of them.

In this case, the sample may be blood, and the filtered substance may be plasma.

A collecting portion 29 may be further formed at one side of the body portion 22 (or below the body portion 22) by cutting some parts of the body portion 22.

Both sides of the collecting portion 29 may be covered with the membrane 26 to form a space.

The filtered substance that moves in the channel 24 due to the force of gravity and/or the capillary force is collected in the collecting portion 29 forming the space.

One end of the outlet passage 27 may pass through the outlet 28 to be connected to the outside, and another end of the outlet passage 27 may be connected to the collecting portion 29.

Accordingly, the filtered substance collected in the collecting portion 29 may be discharged to the outside of the chamber 10 via the outlet passage 27.

In this case, since the outer side surfaces of the pressurizing portion 21 are in close contact with the wall surfaces 16 of the storage space 11, the sample cannot be discharged via the insertion hole 13.

A hydrophilic surface treatment may be performed on the membrane guide 20 so that the filtered substance passing through the membrane 26 may be appropriately collected in the channel 24 of the membrane guide 20 and a capillary force may be appropriately used.

Figure 4:
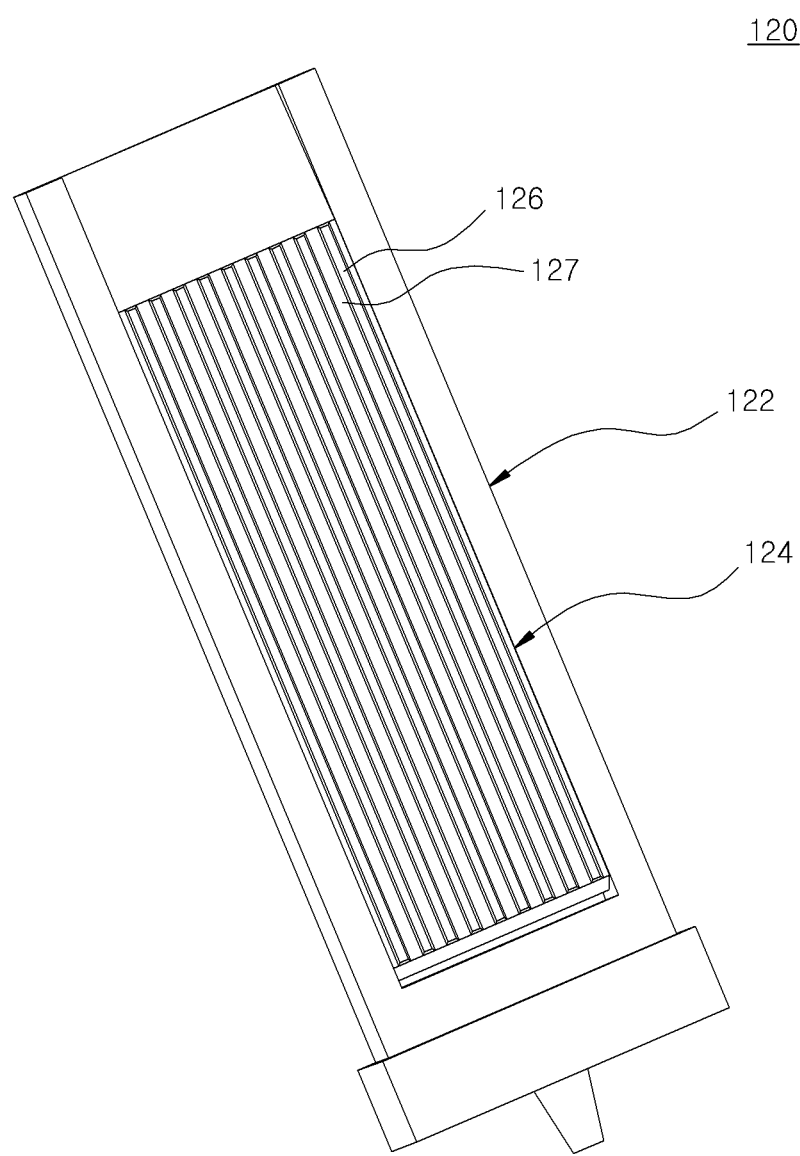
FIG. 4 is a perspective view of a membrane guide of a sampler according to another embodiment of the present invention.

FIG. 4 is a perspective view of a membrane guide 120 of a sampler according to another embodiment of the present invention. As illustrated in FIG. 4, when a channel 124 is a microchannel, a plurality of protrusions 126 and a plurality of grooves 127 may be formed at a bottom surface of the membrane guide 120 in a lengthwise direction of a body portion 122. Through the plurality of protrusions 126 and the plurality of grooves 127, a capillary force may be more effectively applied to stably move a filtered substance.

Figure 5:
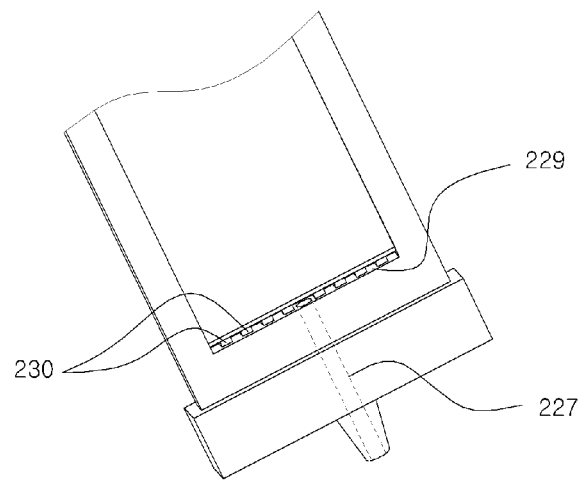
FIG. 5 is a perspective view of a membrane guide of a sampler according to another embodiment of the present invention.
Figure 5:
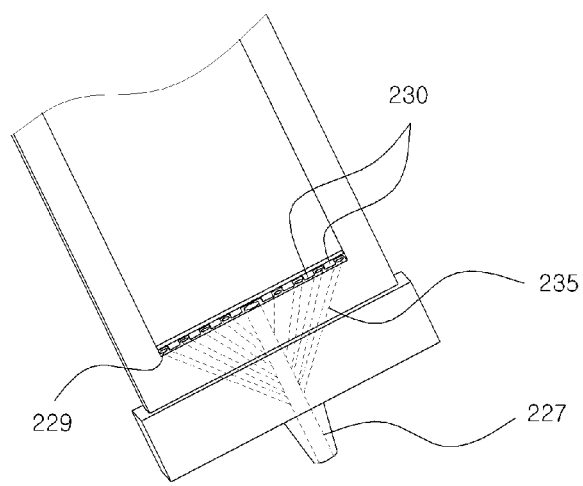

FIG. 5 is a perspective view of a membrane guide of a sampler according to another embodiment of the present invention. Referring to FIG. 5(a), a plurality of pillars 230 may be formed in a collecting portion 229 such that a space of the collecting portion 229 may be filled with the pillars 230.

Here, the pillars 230 may be formed in the collecting portion 229 at predetermined intervals.

Thus, a dead volume of the collecting portion 229 may decrease, and a filtered substance may be effectively introduced into an outlet passage 227 even when the amount of the filtered substance is not large.

Also, as illustrated in FIG. 5(b), an outlet passage 227 may include a plurality of branched channels 235.

In this case, one end of each of the branched channels 235 may be connected to the outlet passage 227 and another end of each of the branched channels 235 may be connected to a collecting portion 229.

Thus, a filtered substance stored in spaces between a plurality of pillars 230 may be introduced into and discharged via the outlet passage 227 through the branched channels 235, thereby more effectively discharging the filtered substance.

Figure 6:
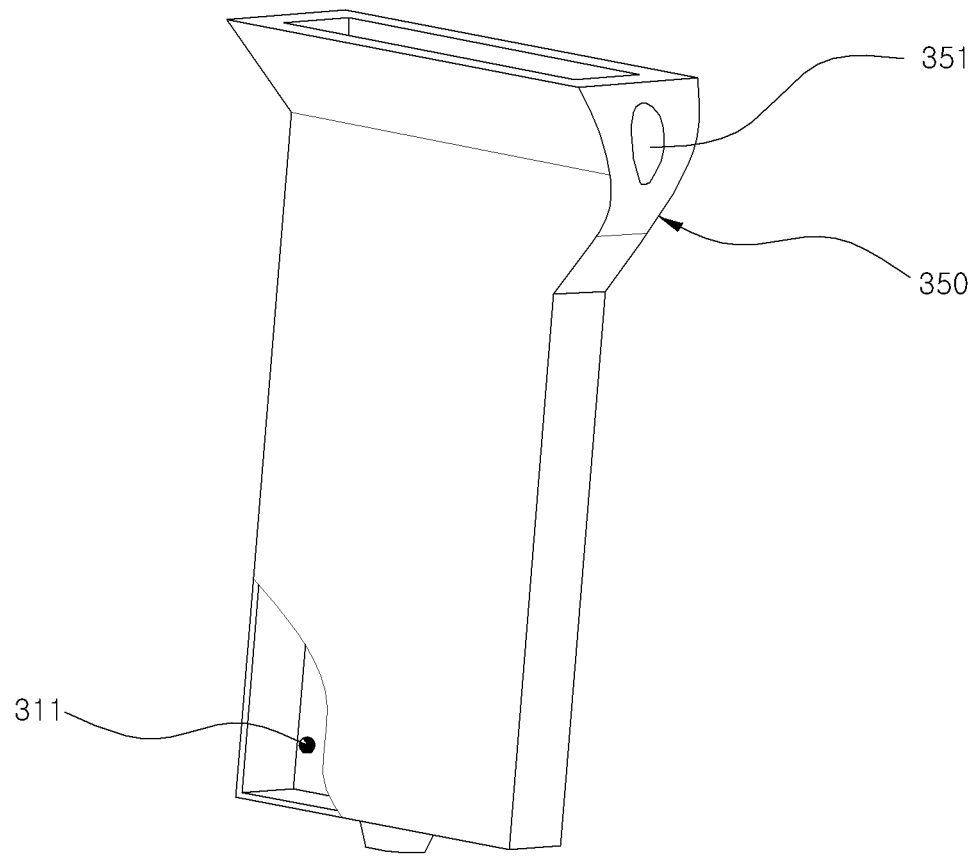
FIG. 6 is a perspective view of a chamber of a sampler according to another embodiment of the present invention.

FIG. 6 is a perspective view of a chamber 310 of a sampler according to another embodiment of the present invention. AS illustrated in FIG. 6, an auxiliary chamber 350 in which a sample is primarily injected before the sample is introduced into a storage space 311 may be further provided at a side of the chamber 310, compared to the samplers according to the previous embodiments.

To this end, inner sides of the auxiliary chamber 350 and the chamber 310 may be connected to each other.

The auxiliary chamber 350 may include a connection portion 351 through which a tube (not shown) or a syringe (not shown) in which a collected sample is stored is directly connected to the auxiliary chamber 350.

With use of the connection portion 351, a process of delivering the sample from the tube or the syringe to the chamber 310 to inject the sample into the chamber 310 may be omitted, thereby easily and rapidly performing a work.

Figure 7:
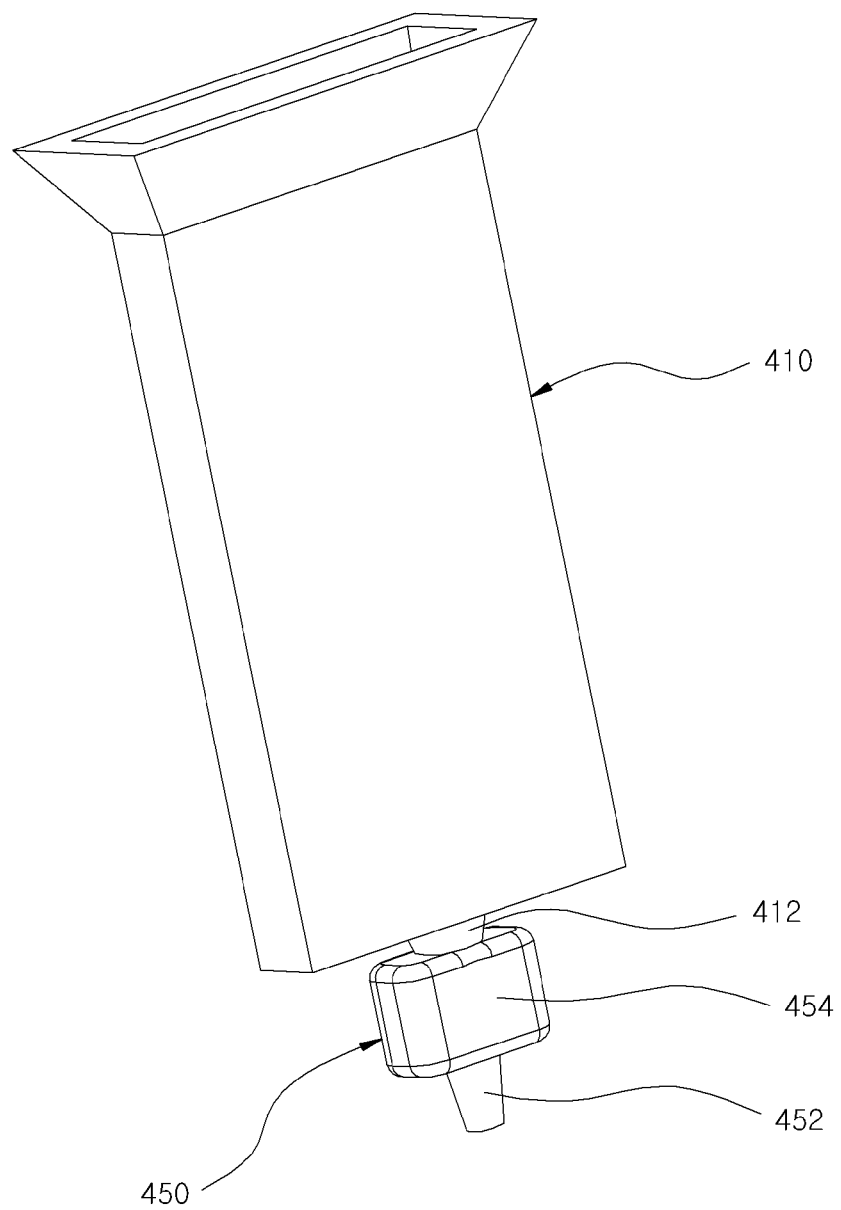
FIG. 7 is a perspective view of a chamber of a sampler according to another embodiment of the present invention.

FIG. 7 is a perspective view of a chamber 410 of a sampler according to another embodiment of the present invention. As illustrated in FIG. 7, a fixed-quantity exhaust chamber 450 may be further coupled to an insertion unit 412 of the chamber 410, compared to the previous embodiments.

The fixed-quantity exhaust chamber 450 may be coupled to the insertion unit 412 such that a space is formed in the fixed-quantity exhaust chamber 450.

Thus, a filtered substance discharged via the insertion unit 412 may be introduced and stored in the fixed-quantity exhaust chamber 450.

The fixed-quantity exhaust chamber 450 may include an exhaust unit 452 via which the filtered substance stored in the fixed-quantity exhaust chamber 450 is exhausted.

A push portion 454 may be further formed on the fixed-quantity exhaust chamber 450. The push portion 454 may be integrally formed with an outer side surface of the fixed-quantity exhaust chamber 450.

Thus, when the push portion 454 is pushed by an external force, pressure in the fixed-quantity exhaust chamber 450 increases and the filtered substance stored in the fixed-quantity exhaust chamber 450 may be thus exhausted via the exhaust unit 452. Otherwise, the chamber 410 may be configured such that the filtered substance is discharged by pushing both side surfaces of the chamber 410 to be pressurized without the push portion 454.

The fixed-quantity exhaust chamber 450 may be detachable from the insertion unit 412. Thus, the fixed-quantity exhaust chamber 450 may be replaced with another fixed-quantity exhaust chamber including an exhaust unit, the diameter of which corresponds to the amount of the filtered substance to be discharged.

Otherwise, the exhaust unit 452 may be coupled to the fixed-quantity exhaust chamber 450 to be detachable from the fixed-quantity exhaust chamber 450, instead of the fixed-quantity exhaust chamber 450. In this case, the exhaust unit 452 may be replaced with another exhaust unit, the internal diameter of which corresponds to the amount of the filtered substance to be discharged.

Whether the fixed-quantity exhaust chamber 450 or the exhaust unit 452 is to be configured to be detachable may be appropriately selected as occasion demands.

Figure 8:
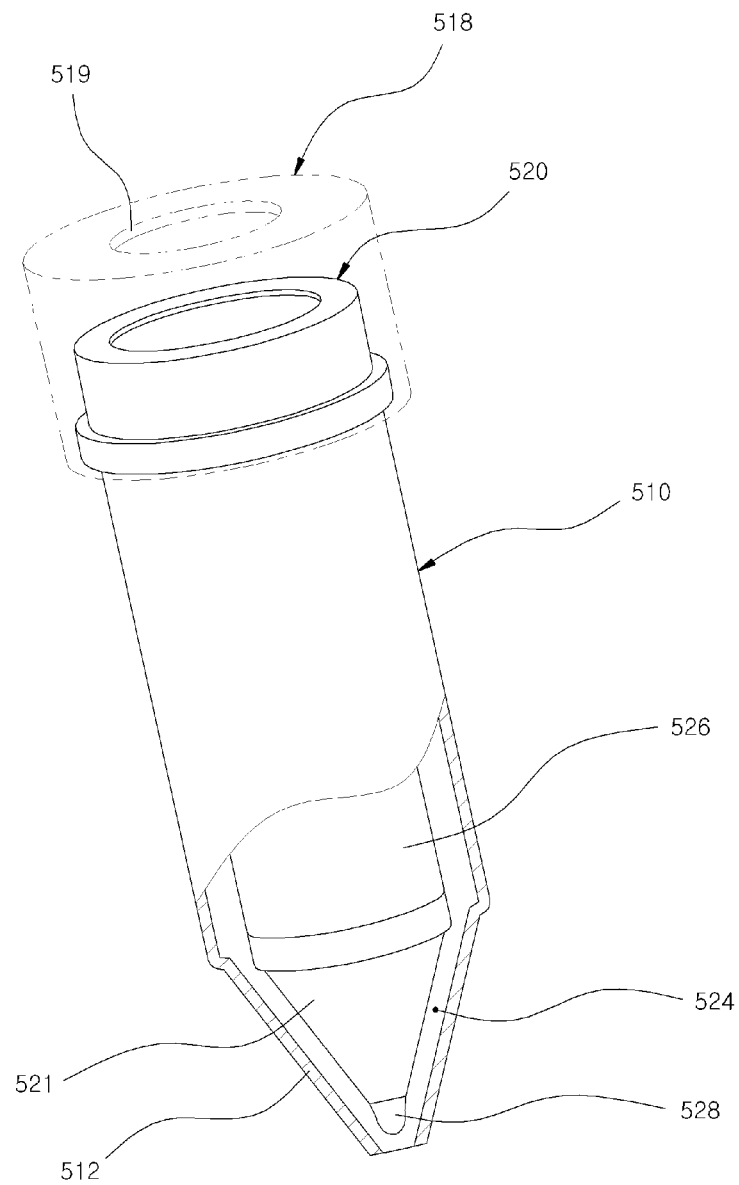
FIG. 8 is a diagram illustrating a state in which a chamber and a membrane guide of a sampler according to another embodiment of the present invention are combined with each other.
Figure 9:
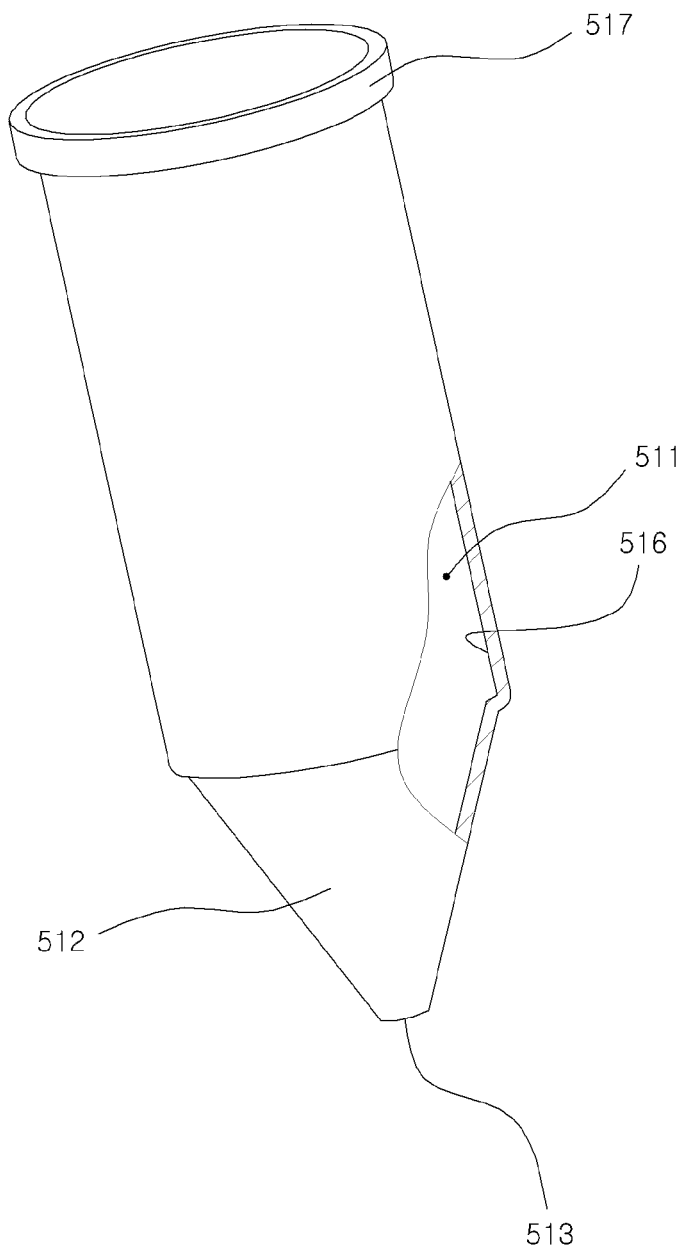
FIG. 9 is a perspective view of a chamber of a sampler according to another embodiment of the present invention.
Figure 10:
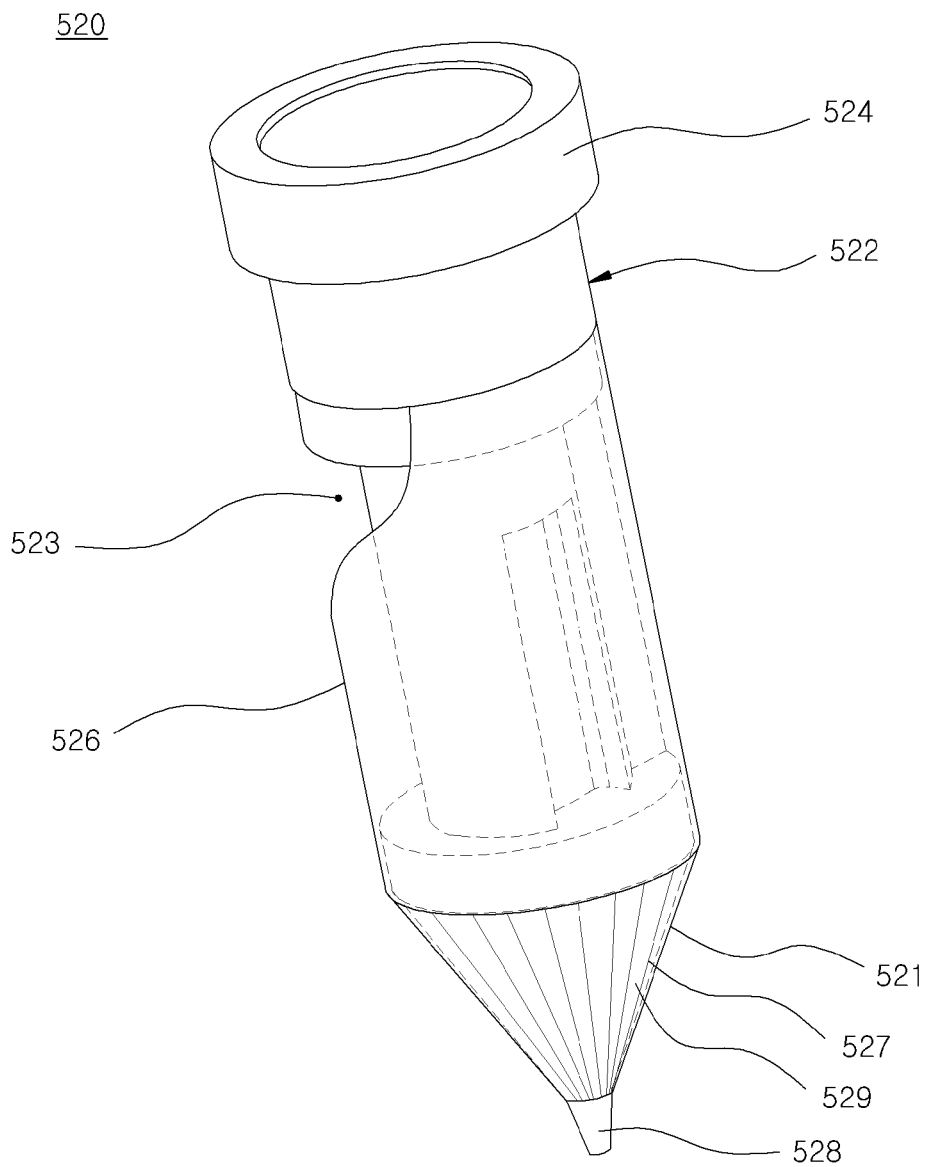
FIG. 10 is a perspective view of a membrane guide of a sampler according to another embodiment of the present invention.

FIG. 8 is a diagram illustrating a state in which a chamber and a membrane guide of a sampler according to another embodiment of the present invention are combined with each other. FIG. 9 is a perspective view of a chamber of a sampler according to another embodiment of the present invention. FIG. 10 is a perspective view of a membrane guide of a sampler according to another embodiment of the present invention.

As illustrated in FIGS. 8 to 10, the sampler may include a membrane guide 520 and a chamber 510.

A storage space 511 is formed in the chamber 510, and an insertion unit 512 is formed at a side of the chamber 510.

The insertion unit 512 may be formed in a tubular shape such that a diameter of the insertion unit 512 becomes smaller in a direction of an end of the insertion unit 512, and an insertion hole 513 may be formed in one end of the insertion unit 512.

Another side of the chamber 510 is open.

The membrane guide 520 is inserted into the storage space 511 in the chamber 510 via the open side of the chamber 510.

The membrane guide 520 may include a body portion 522, a guide portion 521, and a discharging unit 528.

The body portion 522 may be formed to correspond to the storage space 511 and to be spaced a predetermined distance from wall surfaces 516 of the storage space 511 when the membrane guide 520 is inserted into the storage space 511.

Outer sides of the body portion 522 are covered with the membrane 526 to form an inner space 523 in the body portion 522. A sample is stored in the inner space 523.

The membrane 526 may be formed to have multiple holes, the diameters of which become smaller in a direction from the inner space 523 to the outer sides of the body portion 522.

Thus, a substance filtered from the sample stored in the inner space 523 may be discharged to the outside through the membrane 526.

Here, the sample may be blood, and the filtered substance may be plasma.

The filtered substance discharged by passing through the membrane 526 as described above flows into the storage space 511 in the chamber 510. In this case, as described above in the previous embodiments, the sampler that is a combined structure of the chamber 510 and the membrane guide 520 may be placed in a predetermined rack (not shown) in a state in which the sample is injected into the sampler. The filtered substance moves in the direction of gravity in a state in which the sampler is placed on the predetermined rack. In this case, a direction in which the filtered substance passes through the membrane 526 may be set to be different from the direction of gravity as in the previous embodiments.

Also, the guide portion 521 may be formed at a side of the body portion 522 to correspond to the insertion unit 512.

In this case, the guide portion 521 may be formed such that outer side surfaces form a predetermined angle with internal side surfaces of the insertion unit 512. Thus, a channel 524 is formed between the guide portion 521 and the insertion unit 512.

Also, the discharging unit 528 may be formed at one end of the guide portion 521.

Here, the discharging unit 528 may be disposed in the insertion unit 512 to be spaced a predetermined distance from the inner side surfaces of the insertion unit 512.

Thus, the filtered substance discharged via the membrane 526 may move in the channel 524 due to a force of gravity and be then discharged via a gap between the discharging unit 528 and the insertion hole 513.

Here, the channel 524 may be a microchannel. In this case, a capillary force is additionally applied to the filtered substance to cause the filtered substance to move. In this case, a plurality of protrusions 527 and a plurality of grooves 529 may be further formed at an outer side surface of the guide portion 521 in a lengthwise direction of the guide portion 521, thereby increasing an effect of the capillary force.

Also, a plurality of protrusions (not shown) and a plurality of grooves (not shown) may be further formed on an inner side surface of the insertion unit 512 in a lengthwise direction of the insertion unit 512, or may be formed only on the guide portion 521 or the insertion unit 512, thereby increasing an effect of the capillary force causing the filtered substance to move.

A flange portion 517 may be formed on the open side of the chamber 510, and a stopper 524 may be formed on another side of the body portion 522.

Here, an external diameter of the stopper 524 may be greater than an internal diameter of the flange portion 517.

Thus, a bottom surface of the stopper 524 may come in close contact with a top surface of the flange portion 517, thereby constantly maintaining a distance between the membrane guide 520 and the chamber 510 that are coupled to each other.

That is, the stopper 524 and the flange portion 517 may be configured such that a distance between inner side surfaces of the discharging unit 528 and the insertion unit 512 is kept constant when the bottom surface of the stopper 524 comes in contact with the top surface of the flange portion 517.

Thus, the insertion hole 513 may be prevented from being blocked, and the filtered substance passing through the membrane 526 may be thus discharged via the insertion hole 513 without blocking the insertion hole 513.

Also, an auxiliary chamber 518 may be coupled to the flange portion 517.

Here, the auxiliary chamber 518 may be formed such that an inner side surface comes in close contact with an outer side surface of the flange portion 517.

The auxiliary chamber 518 may include a connection portion 519 through which a tube (not shown) or a syringe (not shown) storing a collected sample is directly connected to the auxiliary chamber 518.

With use of the auxiliary chamber 518, a process of transferring a sample from the tube or the syringe to the chamber 510 so as to inject the sample to the chamber 510 may be omitted, thereby easily and rapidly performing a work.

Figure 11:
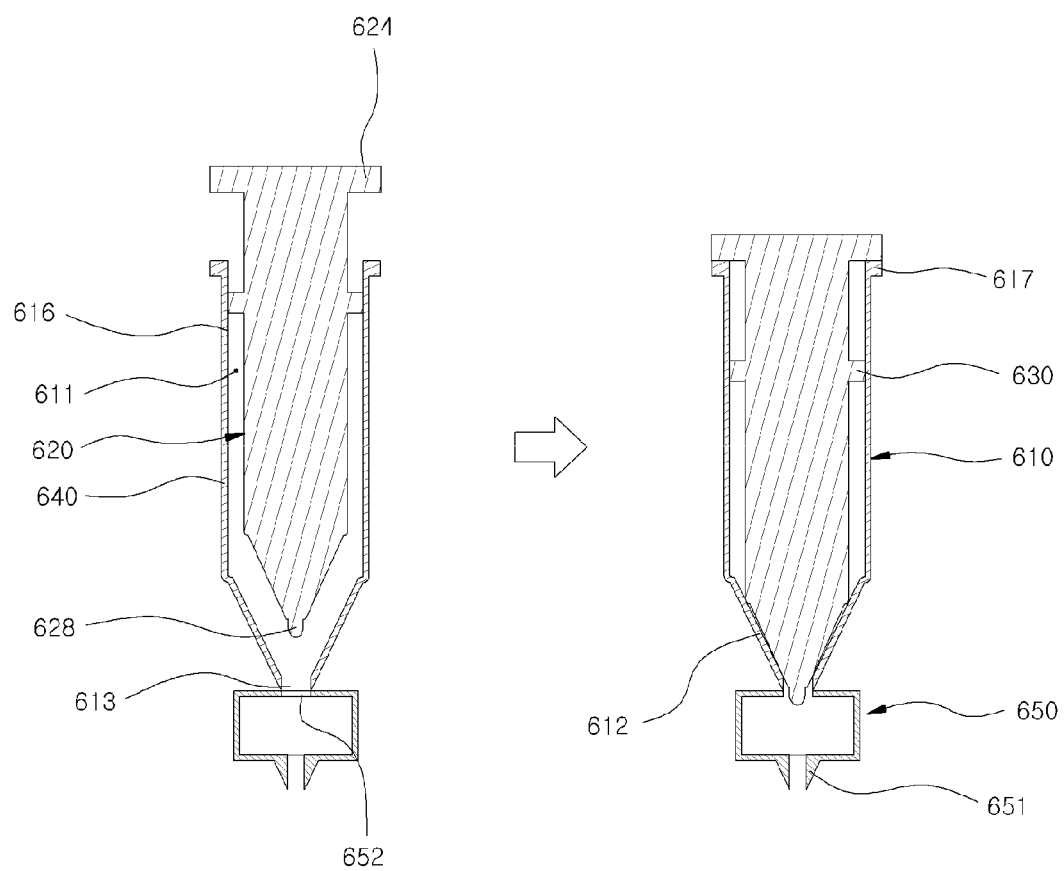
FIG. 11 is a diagram illustrating a state in which a chamber and a membrane guide of a sampler according to another embodiment of the present invention are combined with each other.

FIG. 11 is a diagram illustrating a state in which a chamber 610 and a membrane guide 620 of a sampler according to another embodiment of the present invention are combined with each other.

As illustrated in FIG. 11, a fixed-quantity exhaust chamber 650 may be coupled to an insertion unit 612 of the chamber 610.

Here, an exhaust unit 651 may be formed at a side of the fixed-quantity exhaust chamber 650, and a through-discharge film 652 may be formed in the fixed-quantity exhaust chamber 650.

Thus, when a discharging unit 628 of the membrane guide 620 sequentially passes through an insertion hole 613 of the chamber 610 and the through-discharge film 652, a filtered substance may be introduced and stored in the fixed-quantity exhaust chamber 650.

In this case, pressurizing portions 630 may be formed on the membrane guide 620 so that outer side surfaces of the membrane guide 620 may come in close contact with wall surfaces 611 of a storage space 611 in the chamber 610 to air-tightly block an upper portion of the storage space 611.

Thus, when a push portion 640 that is integrally formed with an outer side surface of the chamber 610 is pressed by an external force, pressures in the chamber 610 and the fixed-quantity exhaust chamber 650 may increase to discharge a fixed amount of the filtered substance stored in the fixed-quantity exhaust chamber 650. In this case, the push portion 640, i.e., an external wall of the chamber 610, may be formed of a flexible material.

Here, movement of the membrane guide 620 is stopped when a stopper 624 comes in close contact with a flange portion 617 of the chamber 610.

The fixed-quantity exhaust chamber 650 may be detachable from the insertion unit 612. Thus, the fixed-quantity exhaust chamber 650 may be replaced with another fixed-quantity exhaust chamber including an exhaust unit, the diameter of which corresponds to the amount of the filtered substance to be discharged.

Figure 12:
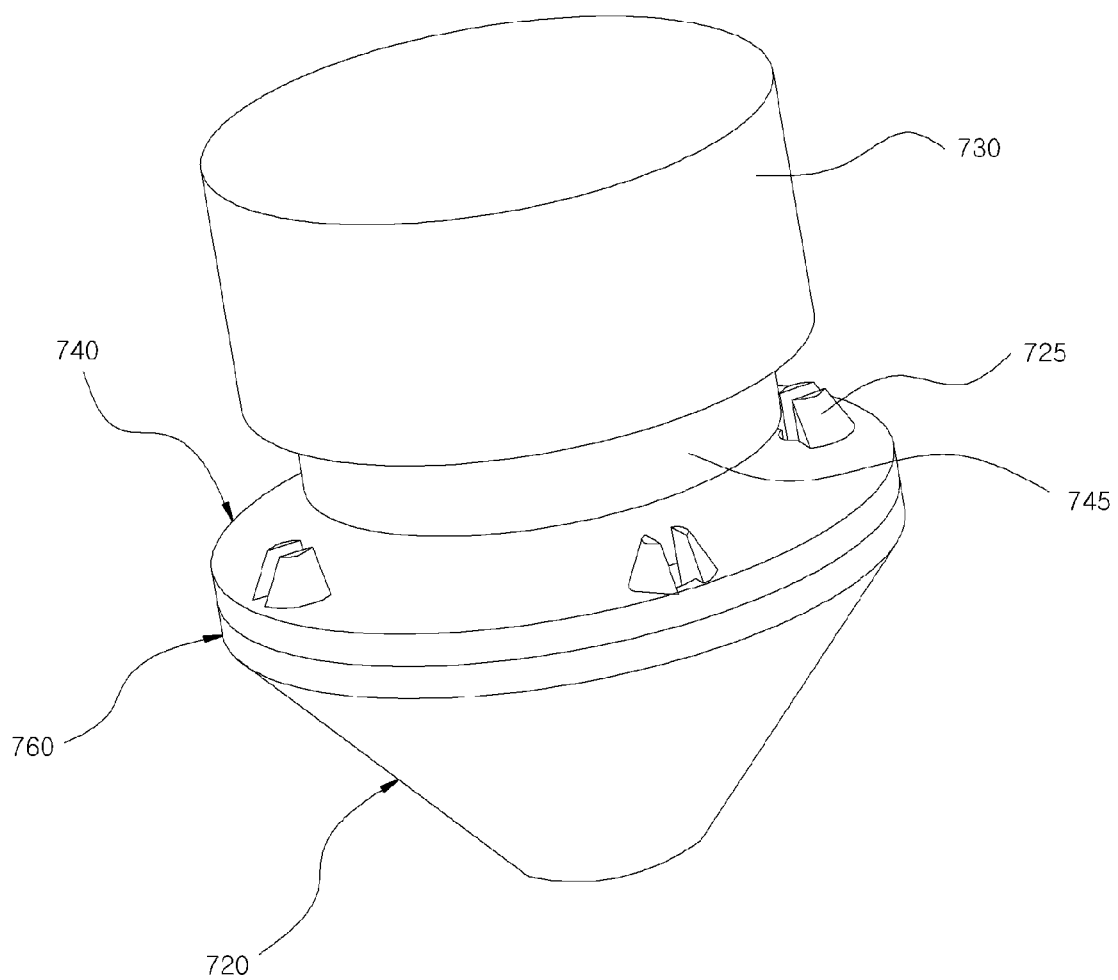
FIG. 12 is a perspective view illustrating a state in which a chamber and a membrane guide of a sampler according to another embodiment of the present invention are combined with each other.
Figure 13:
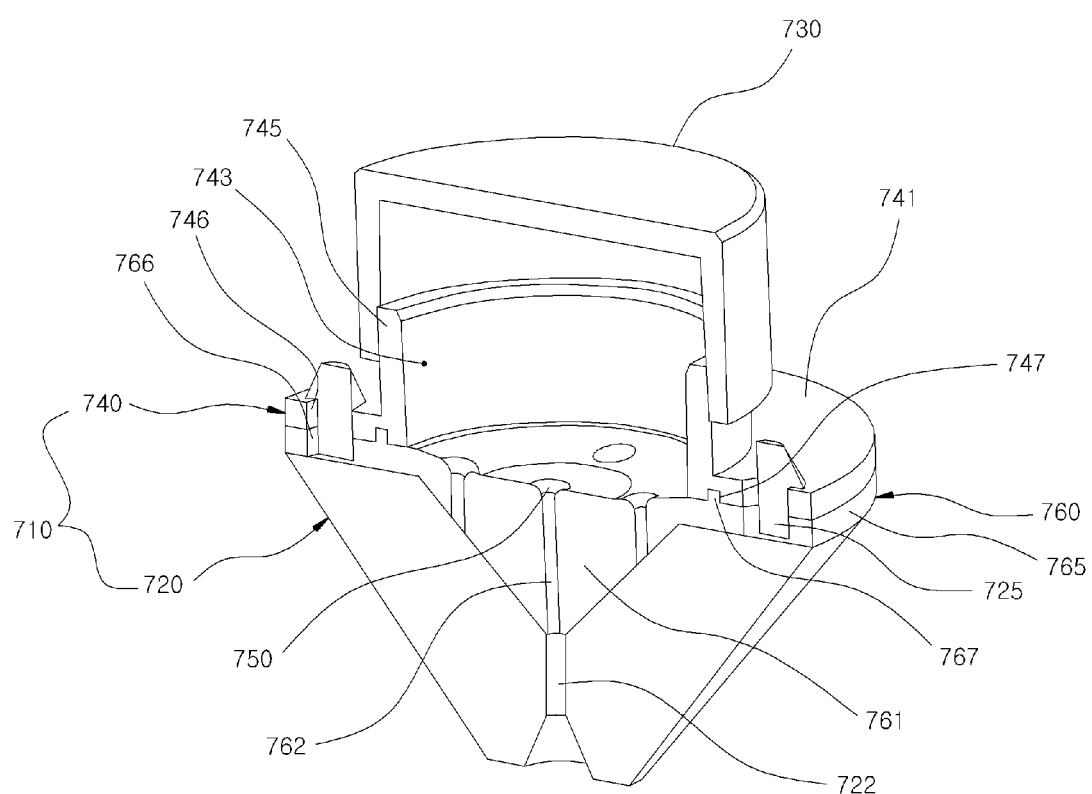
FIG. 13 is a cross-sectional view illustrating a state in which a chamber and a membrane guide of a sampler according to another embodiment of the present invention are combined with each other.
Figure 14:
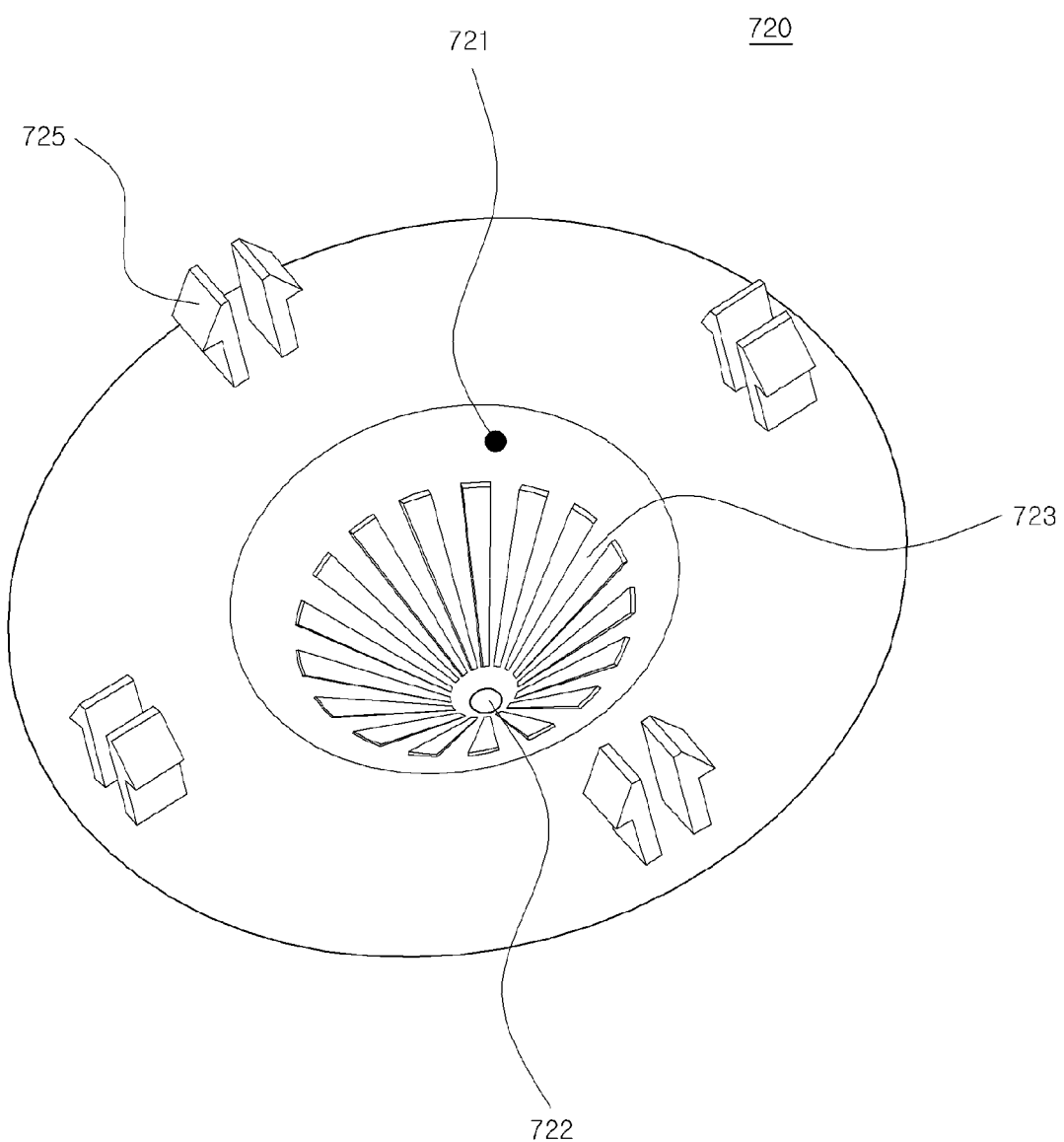
FIG. 14 is a top perspective view of a first chamber of a sampler according to another embodiment of the present invention.
Figure 15:
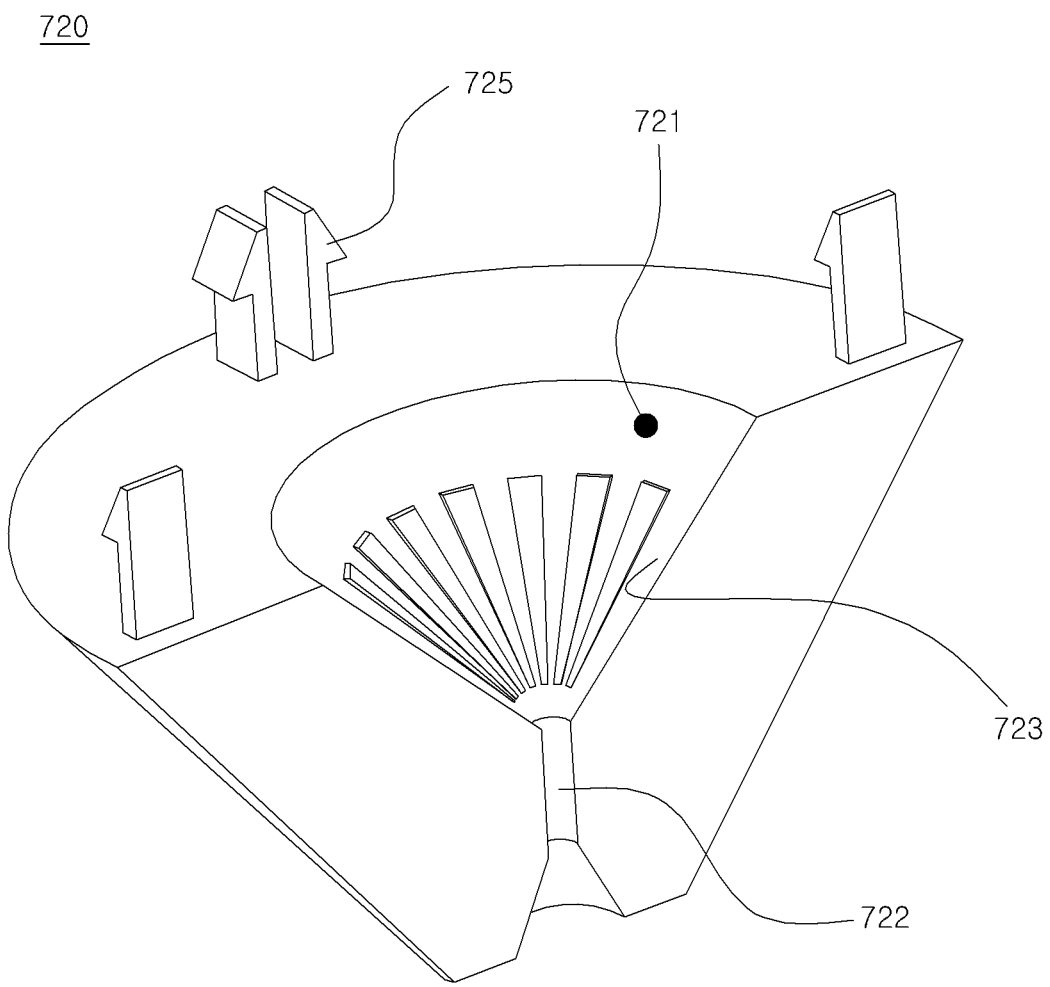
FIG. 15 is a cross-sectional view of a first chamber of a sampler according to another embodiment of the present invention.
Figure 16:
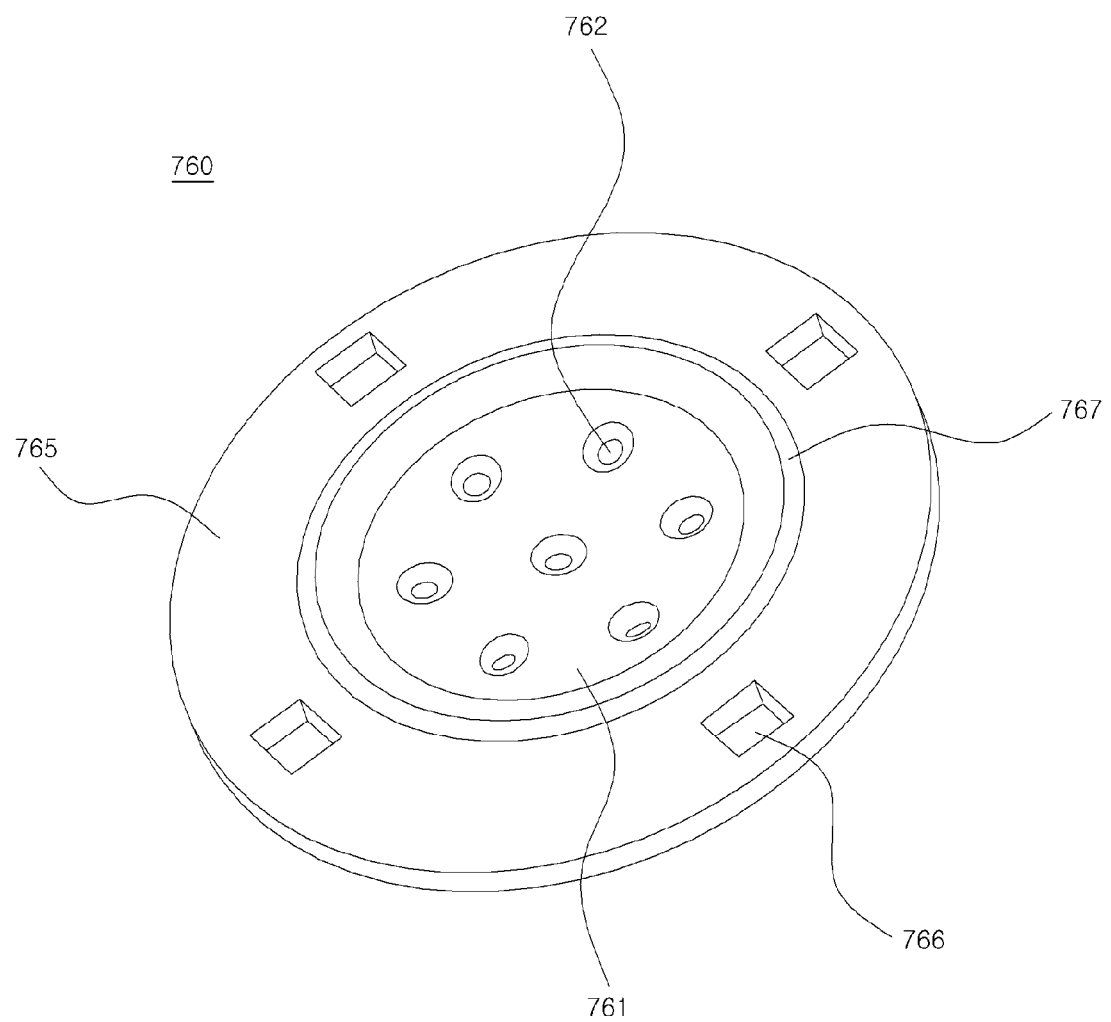
FIG. 16 is a top perspective view of a membrane guide of a sampler according to another embodiment of the present invention.
Figure 17:
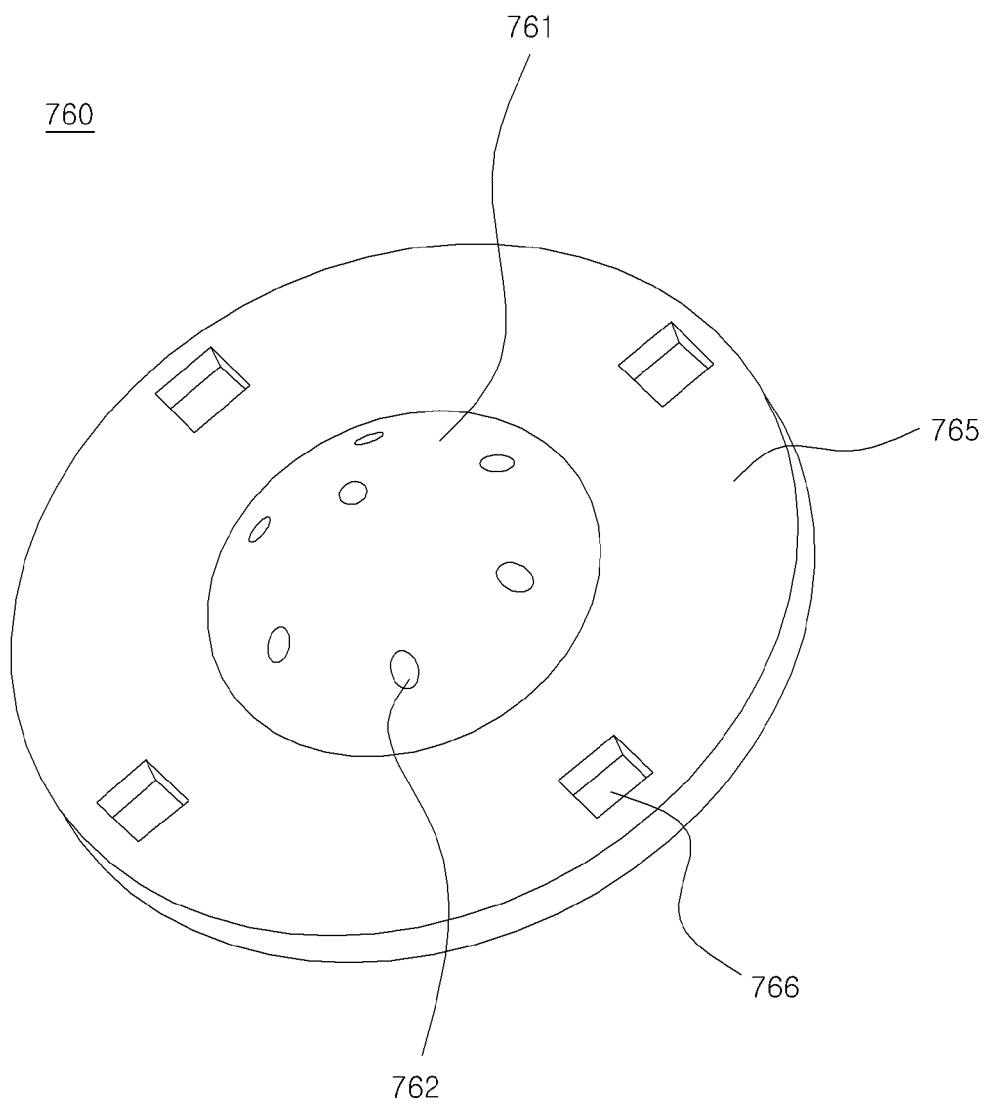
FIG. 17 is a bottom perspective view of a membrane guide of a sampler according to another embodiment of the present invention.
Figure 18:
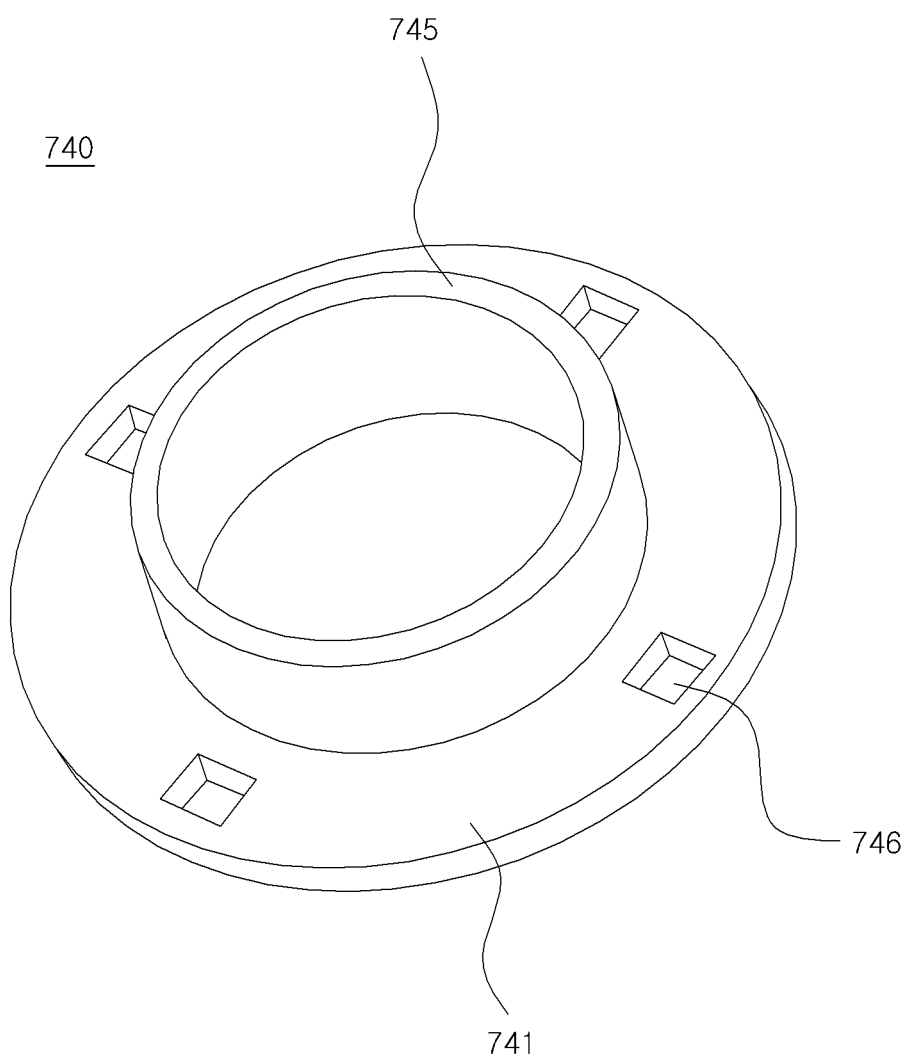
FIG. 18 is a top perspective view of a second chamber of a sampler according to another embodiment of the present invention.
Figure 19:
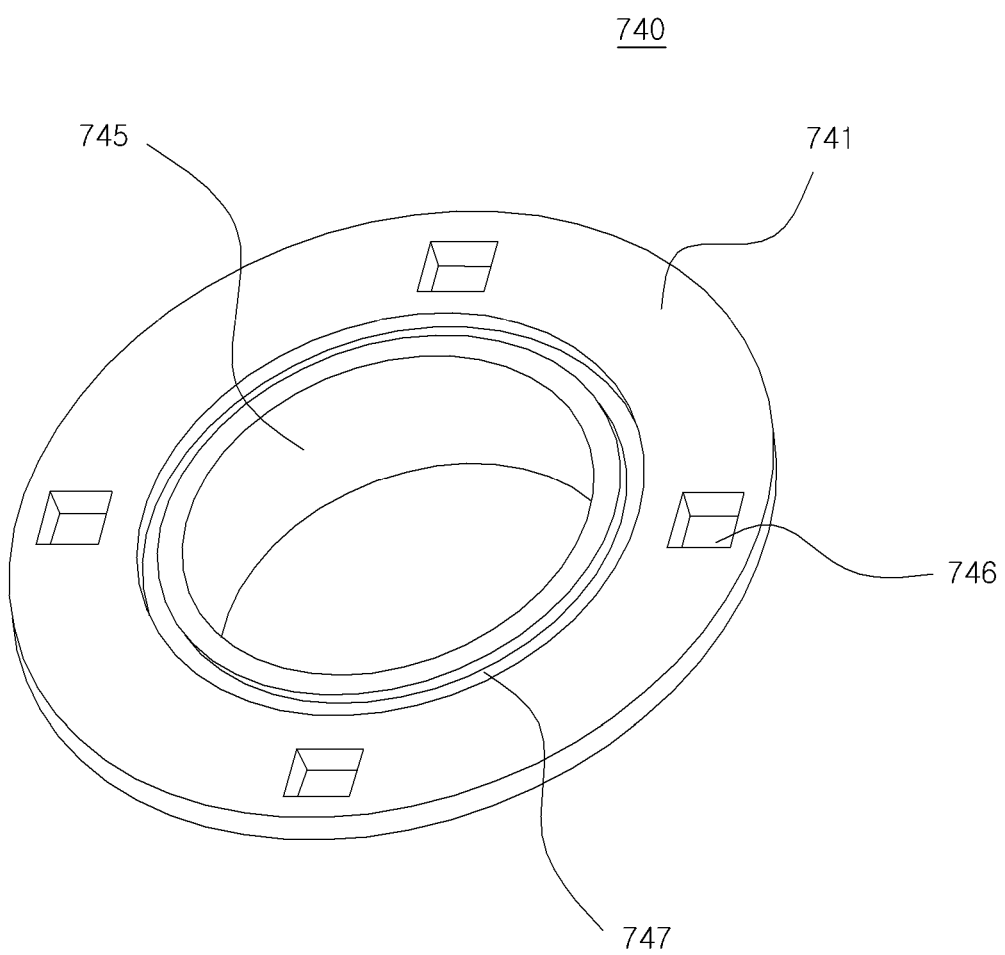
FIG. 19 is a bottom perspective view of a second chamber of a sampler according to another embodiment of the present invention.

FIG. 12 is a perspective view illustrating a state in which a chamber and a membrane guide of a sampler according to another embodiment of the present invention are combined with each other. FIG. 13 is a cross-sectional view illustrating a state in which a chamber and a membrane guide of a sampler according to another embodiment of the present invention are combined with each other. FIG. 14 is a top perspective view of a first chamber of a sampler according to another embodiment of the present invention. FIG. 15 is a cross-sectional view of a first chamber of a sampler according to another embodiment of the present invention. FIG. 16 is a top perspective view of a membrane guide of a sampler according to another embodiment of the present invention. FIG. 17 is a bottom perspective view of a membrane guide of a sampler according to another embodiment of the present invention. FIG. 18 is a top perspective view of a second chamber of a sampler according to another embodiment of the present invention. FIG. 19 is a bottom perspective view of a second chamber of a sampler according to another embodiment of the present invention.

As illustrated in FIGS. 12 to 19, a sampler may include a chamber 710 and a membrane guide 760.

The chamber 710 may include a first chamber 720 and a second chamber 740.

A storage unit 721 is formed to be dented in the first chamber 720, and the discharging unit 722 is formed to pass through the storage unit 721.

A microchannel 723 may be formed on a wall surface of the storage unit 721 in a radial form with respect to the discharging unit 722.

Also, coupling buckles 725 may be formed on an upper surface of the first chamber 720 at predetermined intervals in a circumferential direction.

The second chamber 740 may include a first flange 741 and a tube insertion unit 745. The first flange 741 may be formed in a shape corresponding to an upper side of the first chamber 720, and first coupling holes 746 may be formed in the first flange 741 to be coupled with the coupling buckles 725.

Also, an assembly groove 747 may be formed in a bottom surface of the first flange 741 in a circumferential direction.

The tube insertion unit 745 may be formed to be connected to the inside of the first flange 741, and a storage space 743 may be formed in the tube insertion unit 745 to store a sample.

The tube insertion unit 745 may be formed to become thinner in a direction in which it protrudes. Thus, a tube (not shown) storing a collected sample may be coupled to the tube insertion unit 745 by being screwed into the assembly groove 747.

The tube insertion unit 745 may further include a cover 730 into which a needle (not shown) of a syringe (not shown) storing a collected sample may be inserted.

Thus, even when a sample is collected in a tube or a syringe, the sample may be easily introduced into the storage space 743.

The membrane guide 760 may include a lower dome 761 and a second flange 765.

The lower dome 761 may have a lower surface corresponding to the storage unit 721, and a flat upper surface.

A plurality of capillary tubes 762 may be formed to pass through the upper and lower surfaces of the lower dome 761.

The second flange 765 may extend from the upper surface of the lower dome 761.

In this case, the second flange 765 may be disposed between the first chamber 720 and the first flange 741, and correspond to the first flange 741.

Second coupling holes 766 may be formed in the second flange 765 to correspond to the first coupling holes 746 and to be coupled with the coupling buckles 725.

An assembly protrusion 767 may be formed on the second flange 765 to be coupled with the assembly groove 747.

A membrane 750 may be disposed between the membrane guide 760 and the second chamber 740.

Thus, the sample is stored on an upper surface of the membrane 750.

In this case, the membrane 750 may be configured such that an exterior thereof is engaged with the assembly groove 747 and the assembly protrusion 767.

Also, multiple holes may be formed in the membrane 750 such that the diameters of the multiple holes become smaller from top to bottom, i.e., in a direction from the second chamber 740 to the membrane guide 760.

Thus, some of the sample may be filtered through the membrane 750 and be then introduced downward.

The introduced sample, i.e., the filtered substance, moves to the discharging unit 722 due to a capillary force applied from the capillary tubes 762.

Here, the sample may be blood, and the filtered substance may be plasma.

Figure 20:
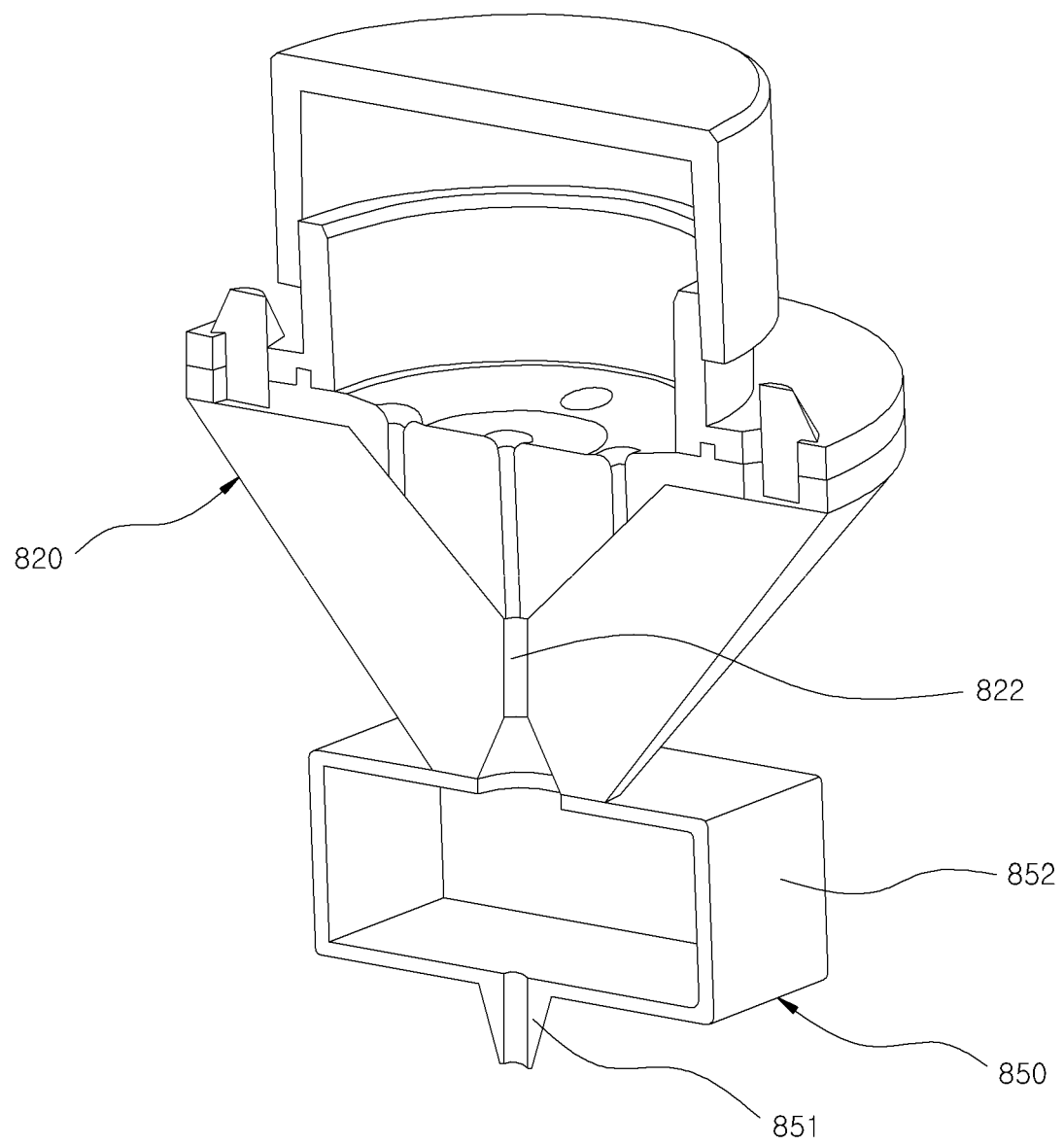
FIG. 20 is a cross-sectional view of a sampler according to another embodiment of the present invention.

FIG. 20 is a cross-sectional view of a sampler according to another embodiment of the present invention. As illustrated in FIG. 20, a lower side of a first chamber 820 may be coupled to a fixed-quantity exhaust chamber 850.

The fixed-quantity exhaust chamber 850 may be coupled to a discharging unit 822 such that an internal space is formed in the fixed-quantity exhaust chamber 850.

Thus, a filtered substance discharged via the discharging unit 822 may be introduced and stored in the fixed-quantity exhaust chamber 850.

The fixed-quantity exhaust chamber 850 may include an exhaust unit 851 via which the filtered substance stored in the fixed-quantity exhaust chamber 850 is exhausted.

A push portion 852 may be further formed on the fixed-quantity exhaust chamber 850. In this case, the push portion 852 may be integrally formed with an outer side surface of the fixed-quantity exhaust chamber 850.

Thus, when the push portion 852 is pressed by an external force, the pressure in the fixed-quantity exhaust chamber 850 increases to discharge the filtered substance stored in the fixed-quantity exhaust chamber 850 via the exhaust unit 851.

The fixed-quantity exhaust chamber 850 may be detachable from the first chamber 820 and be thus replaced with another fixed-quantity exhaust chamber including an exhaust unit, the diameter of which corresponds to the amount of the filtered substance to be discharged.

Otherwise, the exhaust unit 851 may be coupled to the fixed-quantity exhaust chamber 850 to be detachable from the fixed-quantity exhaust chamber 850, instead of the fixed-quantity exhaust chamber 850. In this case, the exhaust unit 851 may be replaced with another exhaust unit, the internal diameter of which corresponds to the amount of the filtered substance to be discharged.

In this case, whether the fixed-quantity exhaust chamber 850 or the exhaust unit 851 is configured to be detachable is not particularly determined and may be appropriately selected.

While the present invention has been particularly shown and described with reference to exemplary embodiments thereof, it will be understood by those of ordinary skill in the art that various changes in form and details may be made therein without departing from the spirit and scope of the invention as defined by the appended claims.

What is claimed is:

1. A sampler comprising:
    a chamber in which an insertion unit having an insertion hole is formed at a side, another side of which is open, and in which a storage space is formed to store a sample; and
    a membrane guide, one side of which is coupled to a membrane positioned inside the chamber and being in parallel to a side wall of the chamber, and which includes a channel in which a substance filtered from the sample stored in the storage space through the membrane moves in the direction of gravity,
    wherein the storage space storing the sample is formed between the membrane and an inner surface of the side wall of the chamber in a direction of a plane of the membrane,
    a direction in which the sample passes through the membrane is perpendicular to the direction of gravity.

2. The sampler according to claim 1, wherein the channel comprises a microchannel, and
    the filtered substance moves due to at least one of a force of gravity and a capillary force.

3. The sampler according to claim 2, wherein the microchannel is formed at a central portion of the body portion in a lengthwise direction of the body portion by forming stepped portions to be stepped at both ends of side surfaces of the body portion in the lengthwise direction of the body portion.

4. The sampler according to claim 3, wherein a plurality of protrusions and a plurality of grooves are formed at a bottom surface of the microchannel in the lengthwise direction of the body portion.

5. The sampler according to claim 3, wherein both ends of the membrane are attached to the stepped portions, respectively, such that the central portion of the membrane is spaced from the microchannel.

6. The sampler according to claim 1, wherein an auxiliary chamber into which the sample is primarily injected before being introduced into the storage space is further connected to one side of the chamber.

7. The sampler according to claim 6, wherein the auxiliary chamber comprises a connection portion to which a tube or a syringe storing a collected sample is directly connected.

8. The sampler according to claim 1, wherein a fixed-quantity exhaust chamber is coupled to the insertion unit, the fixed-quantity exhaust chamber configured to store the filtered substance discharged via the insertion hole, and including an exhaust unit via which the stored filtered substance is exhausted when a push portion is pressed.

9. The sampler according to claim 8, wherein the fixed-quantity exhaust chamber is coupled to the insertion unit to be detachable from the insertion unit, and is replaceable with another fixed-quantity exhaust chamber including an exhaust unit, the internal diameter of which corresponds to an amount of the filtered substance to be discharged.

10. The sampler according to claim 8, wherein the exhaust unit is coupled to the fixed-quantity exhaust chamber to be detachable from the fixed-quantity exhaust chamber, and is replaceable with another exhaust unit, the internal diameter of which corresponds to an amount of the filtered substance to be discharged.

11. A sampler comprising:
    a chamber in which an insertion unit having an insertion hole is formed at a side, another side of which is open, and in which a storage space is formed to store a sample; and
    a membrane guide, one side of which is coupled to a membrane, and which includes a channel in which a substance filtered from the sample stored in the storage space through the membrane moves in the direction of gravity,
    wherein the membrane guide comprises:
    a pressurizing portion formed to correspond to the storage space and including outer side surfaces to be in close contact with the storage space;
    a body portion which is formed at one side of the pressurizing portion, in which the membrane is disposed at both side surfaces thereof to cover the channel, and which is spaced a predetermined distance from wall surfaces of the storage space to allow the sample to pass through the membrane and to be introduced into the membrane guide; and
    a discharging unit formed at another side of the pressurizing portion to be coupled to the insertion unit by being inserted into the insertion unit, and including an outlet passage therein to guide the filtered substance to be discharged.

12. The sampler according to claim 11, wherein, in the body portion, a collecting portion is further formed by cutting some parts of the body portion, the collecting portion including both sides covered with the membrane to form a space in which the introduced filtered substance is collected, and connected to the outlet passage.

13. A sampler comprising:
    a membrane guide in which a sample is stored in an inner space formed by a membrane covering side surfaces of the membrane guide, and that allows a substance filtered from the sample through the membrane to be discharged; and
    a chamber including an internal storage space into which the membrane guide is inserted via another side of the chamber that is open, and an insertion unit having an insertion hole and formed in a tubular shape at another side of the chamber to cause the substance filtered through the membrane to move in the direction of gravity and then be discharged.

14. The sampler according to claim 13, wherein the membrane guide comprises:
- a body portion covered with the membrane to be spaced a predetermined distance from wall surfaces of the storage space;
- a guide portion formed at a side of the body portion to correspond to the insertion unit to form a channel with inner side surfaces of the insertion unit and to guide movement of the filtered substance; and
- a discharging unit extending from an end of the guide portion to be spaced a predetermined distance from an inner side surface of the insertion unit, and configured to guide the filtered substance guided via the channel to be discharged via the insertion hole.

* * * * *